United States Patent [19]
Zakoshansky et al.

[11] Patent Number: 6,057,483

[45] Date of Patent: May 2, 2000

[54] HIGH SELECTIVE METHOD OF PHENOL AND ACETONE PRODUCTION

[75] Inventors: Vladimir Mikhailovitch Zakoshansky, Mt. Vernon, Ind.; Andrei Konstantinovitch Griaznov; Irina Ivanovna Vassilieva, both of St. Petersburg, Russian Federation

[73] Assignee: Illa International, LLC, Reno, Nev.

[21] Appl. No.: 09/148,853

[22] Filed: Sep. 4, 1998

[30] Foreign Application Priority Data

Nov. 3, 1997 [RU] Russian Federation ............ 97118277

[51] Int. Cl.⁷ .......................... C07C 37/08; C07C 37/68; C07C 45/00
[52] U.S. Cl. .......................... 568/798; 568/754; 568/385
[58] Field of Search .................. 568/798, 385, 568/754

[56] References Cited

U.S. PATENT DOCUMENTS 5,254,751  10/1993  Zakoshansky et al. ............. 568/798
5,463,136  10/1995  Blackbourn et al. ............... 568/385

*Primary Examiner*—Paul J. Killos
*Assistant Examiner*—J. Parsa
*Attorney, Agent, or Firm*—Edward Etkin, Esq.

[57] ABSTRACT

Disclosed is a process for the cleavage of technical cumene hydroperoxide (CHP) into phenol, acetone and α-methylstyrene. In a first stage, the CHP cleavage process is conducted in such a way to maintain the heat generation rate and the heat removal rate balanced in each of the CHP cleavage reactors. The cleavage of the CHP is conducted under substantially isothermal conditions at a temperature in the range of 47–50° C. In the second stage of the process dicumylperoxide (DCP) and dimethylbenzene alcohol (DMBA) cleavage is carried out in a multi-section plug-flow reactor under non-isothermal conditions at a controlled temperature increase. The temperature is controlled with the use of thermocouples installed in each section of the reactor. The obtained temperature profile is compared with the temperature profile required by the kinetic model based on ΔT in each section of the reactor. Based on any obtained fluctuations at least one of the amount of water additionally fed to the reactor, the temperature and the degree of sulfuric acid conversion into $NH_4HSO_4$ are adjusted.

31 Claims, 3 Drawing Sheets

HIGH SELECTIVE METHOD OF PHENOL AND ACETONE PRODUCTION

BACKGROUND OF THE INVENTION

This invention relates to the field of petrochemical synthesis, and in particular, to a method of production of phenol, acetone and alpha-methystryrene (AMS) by the cumene method.

There are a number of methods known to produce phenol and acetone by using acidic cleavage of technical cumene hydroperoxide (CHP). The main difference between the known methods is in using different reaction mediums and alternate techniques for removing the heat (380 Kkal/kg) generated during the process of CHP cleavage.

In these prior art processes the best selectivity is obtained by using an equimolar mixture of phenol and acetone as a reaction medium. On a relative basis, 15–30% of acetone, based on technical CHP, is added to this mixture. This is illustrated in Russian Application No. 9400736/04/007229 dated Mar. 1, 1994 and U.S. Pat. No. 4,358,618. This allows one to obtain a good process selectivity as determined by the yield of the desired by-product, AMS, formed from dimethylbenzene alcohol (DMBA) present in technical cumene hydroperoxide. The obtained AMS yield in is about 80%.

During the CHP cleavage, the heat generated is removed. In the process according to U.S. Pat. No. 2,663,735 the heat is removed by acetone evaporation and acetone recycle to the reactor. The generated heat can also be removed by the use of a cooling medium such as cooling water.

During the adiabatic cleavage of 100% CHP the temperature is increased to about 700° C. under the influence of an acidic catalyst. The heat is generated spontaneously. Because of the rapid heat release, the CHP cleavage process is considered very dangerous. Consequently, the combination of heat generation and heat removal is of high priority for improving process safety.

In the process of U.S. Pat. No. 2,663,735, the reaction heat is removed by acetone evaporation and the heat generation and the heat removal are fully combined. The heat generated in the process of cleaving 1 ton of CHP requires feeding approximately 2.2–3 tons of acetone to the reactor. The evaporated acetone is to exhausted from the reactor, condensed and continuously recycled to the reactor. As a result, the reactor is operated in a heat stable manner as is required for process safety.

However, the heat stable condition is obtained only by the use of a comparatively high sulfuric acid concentration of 1200–1300 ppm. However, the high $H_2SO_4$ concentration, which is needed due to the large amount of acetone fed into cleavage products, decreases the activity of sulfuric acid which is the CHP cleavage catalyst. Thus, high acid concentration results in a low yield of desired products and a high content of microimpurities (about 1500 ppm) such as mesithyl oxide, hydroxyacetone, and 2-methylbenzofurane which substantially adulterate the phenol quality. While the process chemistry requires a low sulfuric acid concentration of about 100–300 ppm, this can not be achieved in practice since CHP accumulates in the reactor bottoms because of the sharp decrease of the CHP cleavage rate that results in a large heat release. i.e. when decreasing the sulfuric acid concentration the reactor is operated under unstable heat conditions. Actually the process achieves thermal stability only at a high sulfuric acid concentration but this results in a low process selectivity. Therefore, in the process employing acetone evaporation, the objectives of heat stability and obtaining a high process selectivity are in irreconcilable conflict.

In the processes of the above referenced Russian application, U.S. Pat. Nos. 4,358,618 and 5,254,751, reaction heat is removed with the reaction products or reaction cleavage mass (RCM) by multiple circulations through water cooled heat exchangers. The heat exchangers, which may number from 2 to 6, are in fact the reactors wherein the CHP cleavage occurs. The heat stability of the process (i.e. the process safety) depends on the composition of the reaction products, the range of the acid concentration, the temperature profile and, hence, CHP conversion distribution in the reactors. The process stability deteriorates at higher CHP conversion in the first reactor and as the temperature difference between the first and the subsequent reactors increases. In practice, the more the conditions of the process are non-isothermal, the more precarious is the process state.

In the process according to the Russian application, the CHP and DCP cleavages are performed in two stages. CHP cleavage reactors (mixing reactors) and the DCP conversion reactor (plug-flow reactor) are operated at the same pressure.

The CHP and DCP cleavage are performed in an equimolar mixture of phenol and acetone containing up to 12 wt % of cumene. To reduce the acidic properties of the sulfuric acid and, therefore, to increase the yield of such desired products as phenol, acetone and AMS, additional acetone is added into the reaction products according to the following algorithm:

$$G_{ac.} = G_{CHP} \times 0.125 \ [CHP] + 35/(G_{CHP} \times [CHP]),$$

where:
  $G_{ac.}$, $G_{CHP}$ represent the flow rate of additional acetone and technical CHP, respectively, in kg/hr and
  [CHP] is CHP concentration of technical grade CHP (wt %)
that is equal to 12–14% rel. of acetone based on technical CHP feed rate.

CHP conversion, depending on the feed rate, is maintained in the first reactor at 62–75%, in the second reactor at 87–94% and in the third reactor at 94–98%. The corresponding temperatures in these reactors are 67–79° C., 78–67° C. and 69–60° C., respectively. The above algorithm for the feeding of additional acetone, the temperature, and CHP conversion distribution in the reactors allow the process to operate within a wide range of feed rates.

The CHP concentration at the outlet of the reactors of the first stage is 0.14–0.43 wt.-% that corresponds to a ΔT of 1–3° C. in the calorimeter which controls the first stage of the process Water is fed to the DCP cleavage reactor in an amount so as to provide a water concentration in the reaction products of 1.3–2.0 wt.-%. The operation of the reactor of the second stage is controlled by ΔT equal to 1–3° C. of the calorimeter installed in the line before the DCP cleavage reactor. In the DCP cleavage reactor the process conditions are isothermal. Different temperatures from 94° C. at the low feed rates to 99° C. at high feed rates are maintained in the DCP cleavage reactor. The entire process (1st and 2nd stages) is controlled by the temperature differential between the two calorimeters. This calorimeter temperature differential Δ is 0.2–0.3° C.

In order to reduce non-selective losses in the acetone flash stage, ammonia is added into the line before the evaporator to convert sulfuric acid into the neutral salt $(NH_4)_2SO_4$. As a result, AMS yields of 78.8–79.6% of theory are obtained in the process.

SUMMARY OF THE INVENTION

An object of the present invention is to provide a process to obtain a higher yield of desired products by increasing the AMS yield to 85–87% and reducing chemical losses in the cleavage product rectification columns.

Another object is to increase the process safety by cleaving CHP under conditions which are substantially isothermal.

Further objects of the invention are to reduce the energy consumption in the process by decreasing the amount of recirculating acetone and recuperating the heat with the DCP and DMBA cleavage reactor and to obtain stable DCP conversion in the second stage of the process at variable feed rates and fluctuating operating conditions.

It is a further object of the process of the invention to decrease non-selective losses at the cleavage product rectification stage. These objects, and others, are obtained by the process of the invention.

In the process of the invention, technical grade CHP containing DMBA is cleaved to phenol, acetone and α-methylstyrene. Technical grade CHP is introduced into at least the first of a series of at least three sequential reactors wherein the CHP is cleaved under the influence of an acidic catalyst. The reactors are maintained under substantially isothermal conditions in a temperature range of about 47 to 50° C. to produce a product stream containing DCP and DMBA. The product stream is introduced into a cleavage reactor wherein the DCP is decomposed in a non-isothermal operation to a mixture containing at least one of phenol, acetone and α-methylstyrene.

The advantages of the invention are obtained by selection and control of the temperature conditions at the first and second cleavages, the CHP conversion in the reactors of the first stage, the composition of the reaction products, and by changing the algorithm of the reactor control at the second stage of the process.

The process of the invention, similarly to previously known phenol processes, comprises several main stages determining the selectivity of the process in total:

1. Cumene (isopropylbenzene) oxidation with air and/or oxygen to cumene hydroperoxide (CHP);
2. Acidic ($H_2SO_4$) cleavage of the produced CHP; and
3. Rectification of CHP cleavage products by the method of multi-step rectification The process of the invention shows an improvement of process consumption to parameters such as feed consumption value. More specifically, it has an improved CHP cleavage safety by balancing heat generation and heat removal rates and a decrease in steam consumption. The process embodies a new principle of the control over the second stage-dicumylperoxide (DCP) and dimethylbenzene alcohol (DMBA) conversion. It shows a decrease in chemical losses of desired products at the rectification stage obtained by changing the composition of the products at the DCP reactor outlet.

The various features of novelty which characterize the invention are pointed out with particularity in the claims appended to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

In the drawings, wherein like reference characters denote corresponding or similar elements throughout the various figures.

DESCRIPTION OF THE PREFERRED EMBODIMENT

The CHP and DCP cleavage process of the invention may be viewed as having a first and second stage for the purposes of description. In the first stage, CHP is cleaved and DCP is synthesized in mixing reactors. This cleavage is conducted under the influence of an acidic catalyst which is preferably sulfuric acid.

Figure 1:
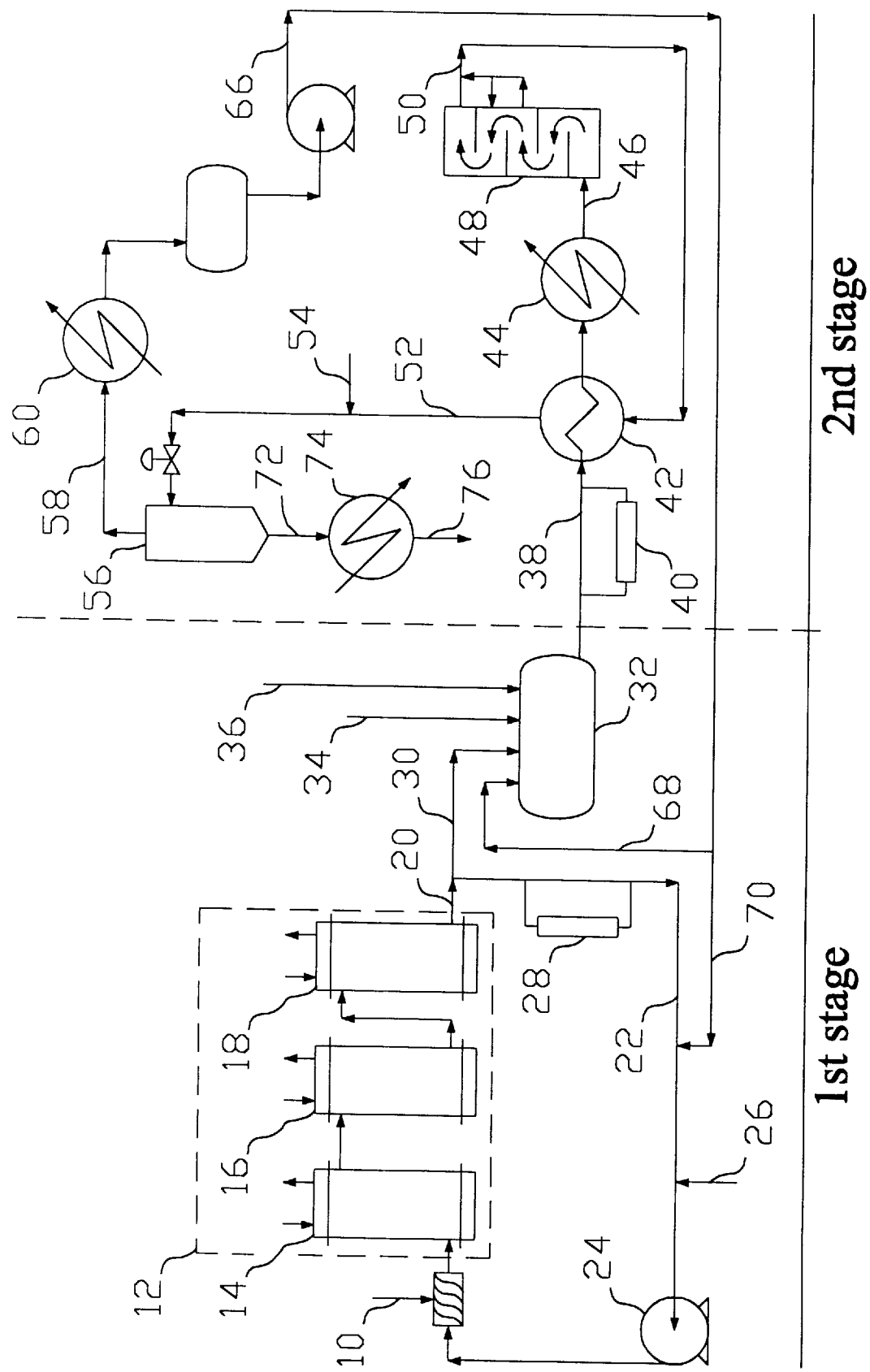
FIG. 1 schematically shows an embodiment of the process of the invention.

Referring to FIG. 1, a feed stream 10 of technical CHP or containing cumene oxidized to CHP in accordance with known prior art processes and containing DMBA is introduced into the first of a cascade of reactors 12. In a preferred embodiment, cascade 12 includes 3 reactors 14, 16 and 18 arranged in series. The reactors 14, 16 and 18 are mixing reactors with respect to byproduct reactions, and plug-flow reactors with respect to CHP decomposition reactions. For this purpose, a series of baffles (not shown) are installed in a shell part of each of the reactors 14, 16 and 18 to enable conversion of the reactors 14, 16, and 18 from mixing regime to plug-flow regime in each section of each reactor. Preferably, 6 to 16 baffles are installed in each reactor.

In the reactors 14, 16 and 18, the CHP is cleaved to form a first product stream 20 containing about 1% CHP, phenol and acetone, about 4–5% DCP to 2–2.5% DMBA, approximately 1–1.5% AMS, and minimal amounts of byproducts—AMS dimers and complex phenols. The cleavage is brought about by the sulfuric acid which is at a concentration in the reaction products of not lower than 180 ppm and not higher than 200 ppm. The first product stream 20 exiting from reactor 18 is divided and a portion of that stream is recycled through line 22 to a pump 24 from which material is forwarded to reactor 14 after being combined with technical grade CHP feed stream 10. The relative quantity of the recycled fraction of stream 20 to stream 10 is about (8–40):1. Sulfuric acid 26 can be introduced in recycle line 22.

Additional acetone is fed to the first stage of the process. The amount of additional acetone is based on the technical CHP flow rate and is maintained within the range of 5–8% relative to the CHP flow rate to reach the required value of CHP conversion at varying feed rates and fluctuating operating conditions. The amount of additional acetone fed should not exceed 8%.

The CHP conversion in reactors 14, 16 and 18 in series is maintained at 42–50%, 67–73% and 78–82%, correspondingly. The temperature in each of the reactors 14, 16 and 18 is maintained between 47 and 50°. Cooling water removes heat generated in the process. Preferably the temperature in reactor 14 is 47–50° C., in reactor 16 is 50–48° C., and in reactor 18 is 48–50° C. That is to say that unlike the prior art, as illustrated by the above cited Russian application and U.S. Pat. No. 5,254,751, the process conditions in the process of the invention are isothermal or at least substantially isothermal in reactors 14, 16 and 18. The above distribution of CHP conversion and temperature in the reactors enables one to balance the heat generation rate and heat removal rate by controlling the CHP cleavage rate. This balance results in a system wherein the heat is stabilized in all points of the reactors, thus promoting process safety.

A substantially isothermal operation in reactors 14, 16 and 18 is obtained by operating with certain amounts of additionally fed acetone, certain water concentrations in the reaction products and obtaining a lower acid concentration in the reaction products. The combination of the above features results in a certain CHP cleavage rate, and, as a result, certain heat generation in each of the reactors 14, 16 and 18 in the first stage. Due to different cooling water flow rates to the first stage reactors, conditions at, or close to, isothermal are maintained. When ΔT1—the difference between exit and entry temperatures of a flow calorimeter 28—deviates from the required temperature by 8–9° C., the temperature is corrected in the first reactor which maintains the required CHP conversion value, and, as a result, the temperature after the first reactor. The temperature after the last reactor of the first stage is also maintained by controlling the cooling water flow rate. Also cooling water is fed to the tube space of the second reactor but that flow rate is preferably kept stable at constant CHP feed rate. Such a method of operation provides conditions which are isothermal or substantially isothermal in the first stage CHP cleavage reactors.

An advantageous aspect of the process of the invention is that it eliminates the increased temperature zones in the reactors that occurs in the conventional prior art cleavage methods. The rate of formation of undesired byproducts, such as AMS dimers and complex phenols, is decreased thus resulting in an increase of the CHP cleavage stage selectivity, and, as a result, the total process selectivity.

The system for performing the process includes a temperature measuring arrangement which in FIG. 1 is illustrated as the calorimeter 28.

The remaining non-recycled portion 30 of the product stream 22 is introduced into an intermediate vessel 32. Water 34 and a base 36, which is preferably NH$_4$OH, are mixed with the product stream 30 in vessel 32. As indicated, a temperature measurement is made by a temperature measuring device 40 shown as a calorimeter in the tank discharge line 38. The mixed stream in line 38 is heated in preferably two stages by heat exchangers 42 (80–90° C.) and 44 (90–100° C.) so that the stream temperature increases by about 50–55° C.

The heated stream 46 is introduced into a reactor 48 for cleaving of DCP and DMBA dehydration. Reactor 48 is preferably a multi-stage or multi-section plug flow reactor with an internal baffle arrangement forming a plurality of sections or zones within the reactor 48.

In plug flow reactor 48, the main reaction of DCP conversion into phenol, acetone and AMS and the side conversion reaction of DMBA into AMS desired byproduct occur. AMS is a desired product since it can be converted into cumene and then returned to the cumene oxidation stage.

In reactor 48, the temperature of the feed is raised in a controlled manner to a temperature in the range of about 120 to 150° C. and preferably to 140–146° C. The change in reactor 48 is a self-sustaining reaction. Preferably, each section or zone of the reactor 48 has independent temperature control by means of, for instance, a thermocouple and a temperature control feed back and forth system.

A product stream 50 leaves reactor 48, passes through the heat exchanger 42, where it transfers heat to stream 38 and enters evaporator 56 where the evaporation of the additionally fed acetone takes place. Stream 52 leaves across heat exchanger 42 and is mixed with a base, such as NH$_4$OH (54), and is then passed to an evaporator 56 wherein part of the acetone is evaporated along with parts of water, cumene and phenol. The evaporated phase 58 is condensed in condenser 60, separated and the condensed acetone 66 is recycled. A portion 68 of the recycled acetone 66 is introduced into intermediate vessel 32 while portion 70 is mixed with stream 22. The non-evaporated cleavage products 72 are removed from evaporator 56 and cooled in heat exchanger 74 and passed as 76. For acetone added to the first and second stages, crude acetone from the distillation stage end-products of acetone columns (not shown) may be used.

In the first and second stages of the process along with the desired products of the process such as phenol, acetone and AMS, undesired byproducts such as AMS dimers and complex phenols are formed in the reactors.

The formation of byproducts is considered as occurring by the conventional carbon and ion mechanism of acidic and catalytic reactions, i.e. the products are protonized by the AMS double bond to form carbcationite "A"

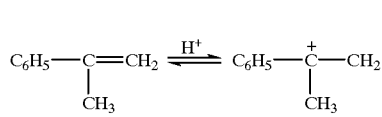

(A)

and further on the conversion of "A" into complex phenols and AMS dimers.

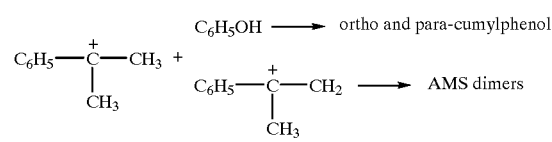

However, it has now been discovered that the reactive particle is not carbony ion but formed oxony ion (B):

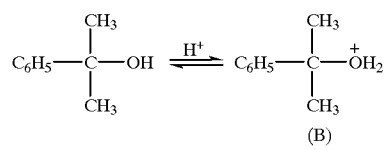

(B)

When phenol and DMBA react with this oxy ion, AMS dimers and complex phenols are formed. Therefore, the reactive particle is not AMS but a DMBA molecule.

The determined reaction mechanism invited further investigation of the conditions of the reaction of DMBA conversion into AMS and DCP. In fact the process equilibrium is recovered:

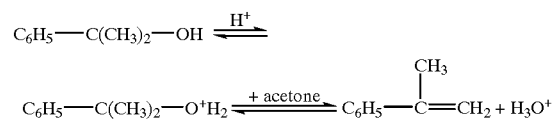

Two important factors, such as solvent composition (i.e. the product composition with regard to the process) and temperature, simultaneously influence the equilibrium between the first and second reactive particles. Having determined the reaction mechanism thereof, we reexamined the conditions of the reaction of DMBA conversion in the DCP reactor.

The shifting of the above equilibrium results in a three to four fold decrease of the amount of unreacted DMBA and the formation of undesired byproducts. It also results in an AMS yield of 85–89.7% of theory under the selected conditions of DMBA and DCP conversion in the second stage of the process. Further, the decrease of DMBA content at the DCP reactor outlet results in a reduction of the amount of undesired products formed in the distillation columns from about 15–17 kg/t phenol to about 8–10 kg/t phenol that is equal to the cumene consumption coefficient decrease by about 7–8 kg/t that is equivalent to economization of initial cumene product of about 80,000 kg per year for every 100,000 tons of final phenol product. The above-described approach of equilibrium shift in the direction of AMS enables reduction of chemical losses during the distillation stage and further enables increase in entire process selectivity in particular due to reduction in non-selective chemical losses during the distillation stage.

Our studies show that the equilibrium DMBA Δ AMS is established very quickly. Simultaneously, DMBA reacts to form AMS dimers and complex phenols. The formation rate of the dimers and complex phenols is slower than the first reaction but increases substantially when the temperature is increased. Thus, there is an adverse competition between these reactions in that, when the temperature is increased the equilibrium is shifted to desired AMS product but also, the amount of undesired products, such as AMS dimers and complex phenols increases. In order to minimize formation of dimers and complex phenols while improving the yield of AMS, the cleavage process in the DCP reactor is conducted in such a manner that the average temperature of the reaction in the DCP reactor is not maintained close to the maximum temperature but is preferably maintained such that the average temperature in the reactor or within a number of zones is lower for example, preferably about 15° C. lower, than the maximum temperature reached in the reactor. On the other hand, the temperature should not be raised in the respective zones at too slow a rate since this also interferes with production of the desired end product. The actual temperature curve depends on the quantity of DCP and DMBA which is a function of the selectivity of the first stage. Higher concentrations of DCP shift the curve.

It has also been found that the heat effect of the DCP cleavage is 214 Kcal/kg. Using the determined heat release of the reaction the process of DCP cleavage is conducted under non-isothermal conditions as shown in FIG. 2.

Figure 2:
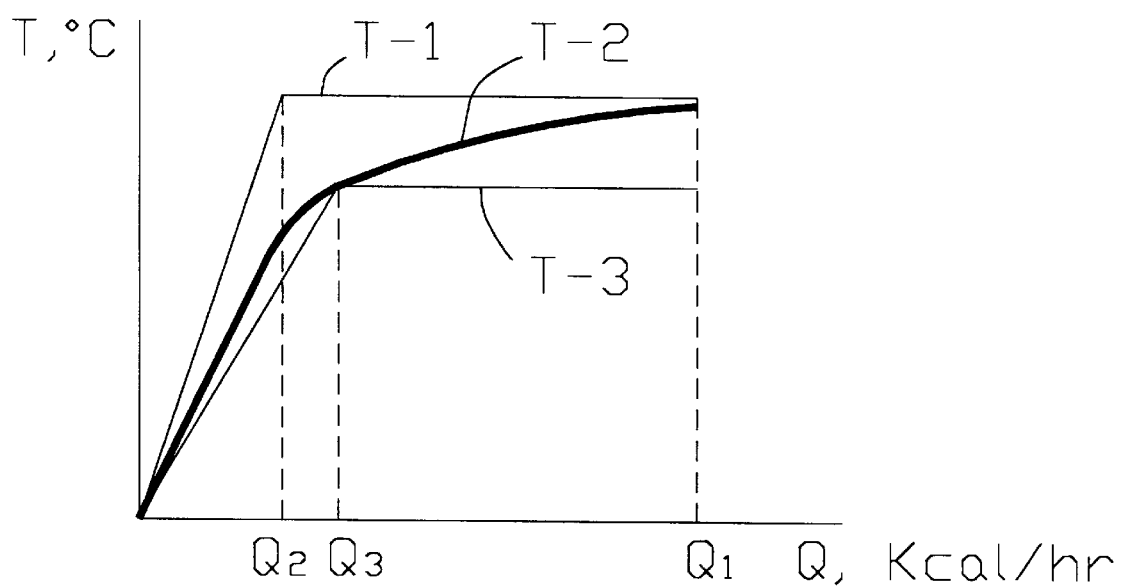
FIG. 2 shows the change of temperature profile in the DCP reactor depending on the amount of heat generated by the cleavage products.

Depending on the amount of heat generated by the cleavage products in heat exchanger 44 (see FIG. 1), the temperature profile in the DCP reactor may be different, i.e. essentially isothermal (curve T-1), non-isothermal (curve T-3) or an intermediate profile (curve T-2) as shown in FIG. 2.

In spite of equal temperatures at the reactor inlet and outlet in the case of T-1 and T-2 (FIG. 2) and in the case of T-2 and T-3 when the average temperature in the reactor is the same, the final results of AMS yield are significantly different. The worst results are obtained for the case of T-1 when the temperature in the reactor 48 is almost constant (i.e. the conditions are isothermal). Under these conditions the AMS yield is about 70% of theoretical.

The best results are obtained when the process operates non-isothermally (see curve T-2) in plug flow reactor 48. The AMS yield is about 89.7% of theory. For the case of T-3 when the average temperature is equal to the T-2 average temperature, results intermediate between isothermal and non-isothermal processes are obtained: AMS yield is about 78–80% of theory.

In a preferred embodiment, a thermocouple is installed in each section of the DCP reactor to maintain the maximal AMS yield in the DCP reactor. The obtained temperature profile is compared to the optimum temperature profile, the latter being based on the developed kinetic model.

Figure 3A:
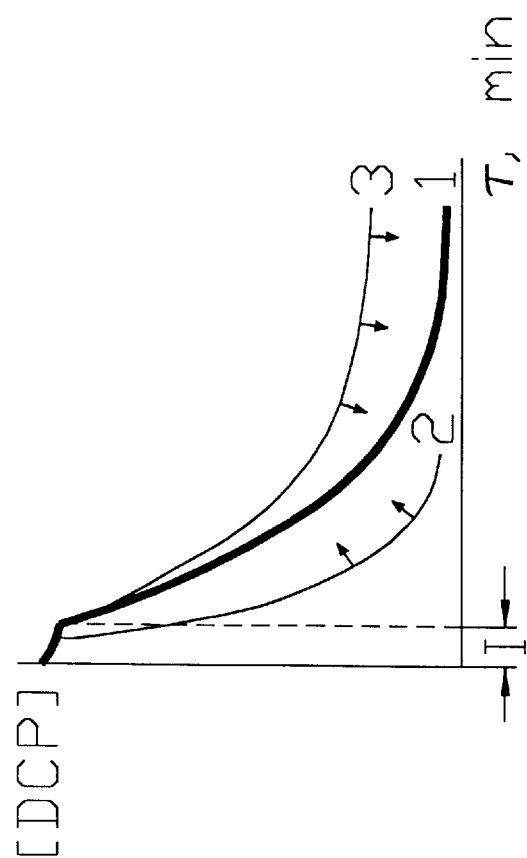
FIGS. 3A and 3B respectively show the dependence of the temperature profile on DCP reactor conditions and the dependence of DCP concentration on DCP reactor conditions.
Figure 3B:
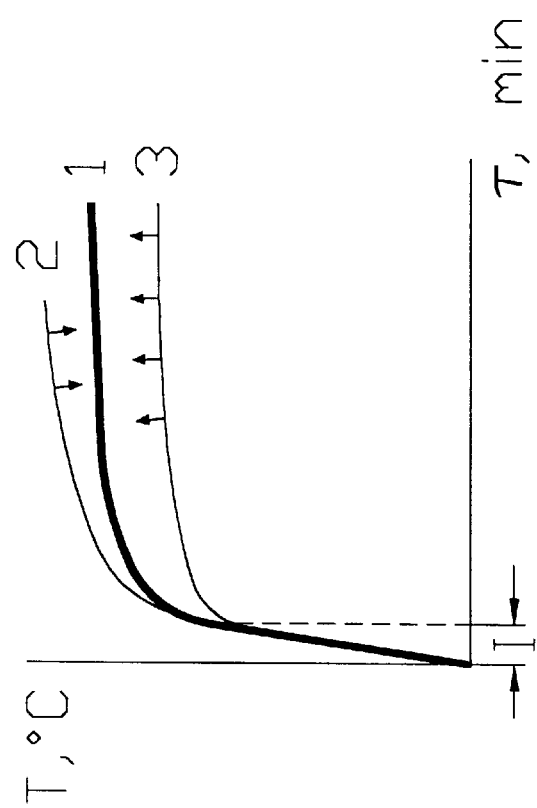

In the case of temperature profile fluctuations when the DCP conversion is incomplete or the DCP conversion exceeds the allowable value, the reactor water concentration is adjusted to return the temperature profile to the initial values, as shown in FIG. 3A. FIG. 3A depicts the dependence of the temperature profile on the DCP reactor conditions, while FIG. 3B depicts the dependence of DCP concentrations on the DCP reactor conditions. In both FIG. 3A and 3B, curve 1 indicates the optimum temperature profile, curve 2 indicates the profile under severe conditions, and curve 3 indicates in FIG. 3A the profile during mild conditions and indicates in FIG. 3B the profile when DCP is converted incompletely. The "I" zone indicates the cleavage product heating zone.

Under the severe conditions of curve 2, FIG. 3B, additional water is fed to the reactor. This decreases the acidic properties of the catalyst and optimizes the temperature profile.

In the case of incomplete DCP conversion (curve 3, FIG. 3B) in the reactor, the amount of water fed to the reactor is decreased and the temperature in the heater installed before the DCP reactor is increased. This results in an increase in the DCP cleavage rate and allows one to obtain the required DCP conversion value.

The process of the invention exhibits numerous advantages over the processor of the prior art. In particular, the inventive process differs from the process described in U.S. Pat. No. 5,254,751 as follows:

1. The CHP cleavage process in the mixing reactors in conducted, due to the balanced heat generation and heat removal rates, i.e. under conditions which are very close to, or are substantially, isothermal. This improves process safety and selectivity.

2. The DCP cleavage process in the plug flow reactor is non-isothermal at a controlled temperature increase from 120 to 146° C. and at the DCP and DMBA conversion depth controlled by changing at the same time the water concentration in the cleavage products and the degree of sulfuric acid conversion into $NH_4HSO_4$ at varying flow rates. Temperature is controlled by installing a thermocouple in each section of the plug flow reactor. The obtained temperature profile is compared to the temperature profile required by the kinetic model. Based on the temperature deviation or Δ value in each section of the reactor and on the fluctuations, the amount of water additionally fed to the reactor, the temperature and the degree of sulfuric acid conversion into $NH_4HSO_4$ are corrected.

3. The composition of reaction environment in the CHP decomposition stage and the DCP decomposition stage is materially different due to the addition of variable quantities of acetone in each of the mentioned stages.

4. Due to the change of the composition of the reaction medium and the change of the algorithm of the reactor control at the second stage of the process the yield of desired AMS yield is increased to 85–89.7% of theory.

The aforementioned advantages and features of the process of the invention are demonstrated by the following examples and are tabulated in the Tables 1 and 2 shown below after the Example descriptions. Example 1 is a comparative example while Examples 2 to 11 are of the process of the invention.

EXAMPLE 1 (COMPARATIVE)

72 t/hr of technical CHP is fed to the reactor block comprising three tube-type reactors installed in series. The reactors are operated at pressures of 2–10 atm. The composition of technical CHP introduced into the reactor series is as follows:

| Component | wt % |
|---|---|
| Cumene hydroperoxide | 82.9 |
| Cumene | 12.0 |
| DMBA | 4.2 |
| Acetophenone | 0.6 |
| Dicumylperoxide | 0.3 |

9976 kg of acetone per hour is added continuously to the circulating cleavage products according to the set algorithm (app.12,16% of the amount of added CHP).

As a result of the addition of acetone, the mole ratio of the reaction products phenol:acetone:cumene is 1:1.42:0.22. Sulfuric acid is added continuously to the circulating cleavage products. The flow rate of sulfuric acid is 21 kg/hr, the sulfuric acid content in the reaction products is 250 ppm, and the flow rate of water is 2 kg/hr.

In the first stage, the CHP conversion is maintained in the first reactor at 65%, in the second reactor 89.6% and in the third reactor at 94.5%. The temperatures in the respective reactors are maintained at 75.8° C., 72.4° C. and 63.1° C.

The CHP concentration at the outlet of the first stage reactors (14, 16, 18) is 0.21 wt.-% that corresponds to a $\Delta T_1$ value of 1.59° C. in the calorimeter by which the first stage of the process is controlled.

The cleavage of DCP formed in circulation loop is conducted in an adiabatic two section plug flow reactor. Water at a flow rate of 716.6 kg/hr is continuously added to the feed line to the DCP cleavage reactor to maintain the water concentration at the reactor outlet at 1.91 wt %.

In DCP cleavage reactor the same composition of reaction products, i.e. the ratio of phenol:acetone:cumene as found in the CHP cleavage products is maintained.

The second stage reactor is controlled by the temperature differential $\Delta T_2$ which is equal to 1.34° C. by the calorimeter installed in the line prior to the DCP cleavage reactor. The process in the DCP cleavage reactor is isothermal at a temperature of 99° C. The overall process ($1^{st}$ and $2^{nd}$ stages) is controlled by the temperature difference between the two calorimeters. That temperature difference based on the calorimeter readings is 0.25° C.

Acetone added to the reaction products at the CHP cleavage stage is removed in the evaporator installed after the DCP cleavage reactor. After being distilled in the evaporator and condensed in the cooler, the acetone is recycled to the CHP cleavage stage.

To decrease non-selective losses of desired products such as phenol and AMS, aqueous ammonia solution is added to the evaporator to convert sulfuric acid into the neutral salt $(NH_4)_2SO_4$.

The AMS yield after the cleavage stage is 78.6% of theory.

EXAMPLE 2

72 t/hr of technical CHP having the composition as in Example 1 is introduced into the mixing reactors in the CHP cleavage stage. The process is as shown in FIG. 1.

The CHP cleavage is indicated in reaction products wherein the mole ratio of phenol:acetone:cumene is maintained as 1:1.28:0.22. This corresponds to 8 rel. % of additionally fed acetone based on technical CHP.

The sulfuric acid flow rate is 16.6 kg/hr. The sulfuric acid concentration in the reaction products is 200 ppm.

In the first reactor, a CHP conversion of 50% is maintained. In the second reactor, the conversion is 69.0% and 81.16% in the third reactor. The temperatures are 48.2° C., 48.3° and 49° C., respectively. The temperature profile in the CHP cleavage reactors is substantially isothermal.

The DCP cleavage is conducted in a multi-section plug flow reactor operating non-isothermally at a controlled temperature increase of from 120 to 137° C. Each section of the reactor is equipped with a system to maintain a set temperature therein.

Water, at a flow rate of 418.9 kg/hr is added continuously to the feed line in the DCP cleavage reactor to maintain a water concentration at the reactor outlet of 1.4 wt % . 57.5 kg/hr of an aqueous 5% ammonia solution is added to provide a sulfuric acid conversion into $NH_4HSO_4$ of 50%.

Acetone, added to the CHP cleavage stage reaction products, is removed in the evaporator which follows the DCP cleavage reactor. Acetone, distilled in evaporator and condensed in the cooler, is recycled to the CHP cleavage stage. To decrease non-selective losses of desired products such as phenol and AMS, an aqueous ammonia solution is added to the evaporator to convert sulfuric acid into the neutral salt $(NH4)_2SO_4$.

The AMS yield after the cleavage stage is 85.6% of theory.

EXAMPLE 3

A CHP cleavage process is conducted in the same manner as in Example 2 with technical CHP of the following composition.

| Component | Wt.-% |
|---|---|
| Cumene hydroperoxide | 90.3 |
| Cumene | 2.0 |
| DMBA | 6.2 |
| Acetophenone | 1.0 |
| Dicumylperoxide | 0.5 |

The CHP conversion in the first reactor is 49.6%, in the second reactor is 67.0% and in the third reactor is 78.9%. The temperatures in the reactors are 48.5° C., 49.5° C. and 50.0° C., respectively.

The DCP cleavage is performed in a multi-section plug flow reactor operating non-isothermally with a controlled temperature increase of from 120 to 143° C. equipped with a system of independent forced maintenance of set temperature in each section.

A continuous water flow of 198.7 kg/hr is added to the feed line in the DCP cleavage reactor to maintain the water concentration at the reactor outlet at 1.4 wt %. An aqueous 5% ammonia solution is added at a flow rate of 60.3 kg/hr to obtain a 50% conversion of sulfuric acid conversion into $NH_4HSO_4$.

The AMS yield after the cleavage stage is 85.1% of theory.

EXAMPLE 4

The process is conducted in the same manner as in Example 2 except that 15.1 kg/hr of sulfuric acid is added to the circulating cleavage products that results in the decrease of $H_2SO_4$ concentration in the CHP cleavage reactors to 180 ppm.

The CHP conversion in the first reactor is 48.8%, in the second reactor is 67.0% and in the third reactor is 79.6%. The temperatures are 48.4° C., 49.1° C. and 49.9° C., respectively.

The DCP cleavage is conducted in a multi-section plug flow reactor operating non-isothermally at a controlled temperature increase of from 120 to 139° C. The reactor is equipped with a system to independently maintain set temperature in each section.

The AMS yield after the cleavage stage is 85.8% of theory.

EXAMPLE 5

A CHP cleavage process is conducted in the same manner as in Example 2 except that the cleavage is conducted in the reaction products keeping the mole ratio of phenol:acetone::cumene as 1:1.19:0.22 that corresponds to 5 rel. % of additionally fed acetone based on technical CHP.

The sulfuric acid concentration in the reaction products is 180 ppm.

The CHP conversion in the first reactor is equal to 50.0%, in the second reactor to 68.8% and in the third reactor to 81.7%. The temperatures are 47.0° C., 48.3° C. and 48.9°, respectively.

The DCP cleavage is conducted in a multi-section plug flow reactor operating non-isothermally at a controlled temperature increase of 120 to 135° C. The reactor is equipped with a system for independently maintaining a set temperature in each section.

The AMS yield after the cleavage stage is 85.7% of theory.

EXAMPLE 6

A CHP cleavage is conducted in the same manner as in Example 4 except that the feed rate is 90 t/hr, i.e. 25% higher than in comparative Example 1.

The CHP conversion in the first reactor is equal to 44.0%, in the second reactor to 67.0% and in the third reactor to 77.1%. The temperatures are 50.0° C., 50.0° C. and 48.6° C., respectively.

The DCP cleavage occurs in a multi-section plug flow reactor operating under non-isothermal conditions at a controlled a temperature increase of from 120 to 137° C. The reactor is equipped with an independent system for maintaining a pre-selected temperature in each section of the plug flow reactor.

The AMS yield after the cleavage stage is 85.6% of theory.

EXAMPLE 7

A CHP cleavage is conducted in the same manner as in Example 4 except that the feed rate is 54 t/hr, i.e. 25% lower than in comparative Example 1.

The CHP conversion in the first reactor is 50.0%, in the second reactor 72.9% and in the third reactor 81.9%. The temperatures are 50.0° C., 49.2° C. and 49.0° C., respectively.

The DCP cleavage is conducted in a multi-section plug flow reactor operating in a non-isothermal condition at a controlled temperature increase of from 120 to 137° C. The reactor is equipped with an independent forced maintenance system of set temperature in each section.

The AMS yield after the cleavage stage is 85.5% of theory.

EXAMPLE 8

A CHP cleavage is conducted in the same manner as in Example 4 except that water, at a flow rate of 886.0 kg/hr, is added into the CHP cleavage products before being feed to the DCP cleavage reactor to keep the water concentration in the DCP cleavage reactor equal to 2.0 wt %.

The DCP cleavage is conducted in a non-isothermal manner at a controlled temperature increase of from 129 to 146° C.

The AMS yield after the cleavage stage is 87.0% of theory.

EXAMPLE 9

The CHP cleavage is conducted in the same manner as in Example 7 except that 629.0 kg/hr of water flow is added to the CHP cleavage products before adding feed to the DCP cleavage to keep the water concentration in the DCP cleavage reactor equal to 1.7 wt %.

The DCP cleavage is conducted non-isothermally at a controlled temperature increase of from 125 to 142° C.

The AMS yield after the cleavage stage is 86.4% of theory.

EXAMPLE 10

A CHP cleavage is conducted in the same manner as in Example 2 except that water, at a flow rate of 886.0 kg/hr, is introduced into the CHP cleavage products before adding the feed to the DCP cleavage reactor to keep the water concentration in the DCP cleavage reactor at 2.0 wt %. The DCP cleavage step is conducted non-isothermally at a controlled temperature increase of from 129 to 146° C.

The AMS yield after the DCP cleavage stage is 86.8% of theory.

EXAMPLE 11

A CHP cleavage is conducted in the same manner as in Example 9 except that 629.0 kg/hr of water and 17280 kg/hr of acetone are added into the CHP cleavage products before the feed is introduced into the DCP cleavage reactor to keep the concentration of water in DCP cleavage reactor at 1.7 wt % and the additional concentration of acetone in DCP cleavage reactor at 24% relative to the CHP introduced into the first stage.

The DCP cleavage is conducted non-isothermally at a controlled temperature increase of from 125 to 142° C.

The AMS yield after the cleavage stage is 89.7% of theory.

The results of the above examples are tabulated in the following Tables 1 and 2.

Example Summary Table 1: 1st Stage - CHP Cleavage

| Exp. No. | Tech. CHP Flow Rate t/hr | Composition of Technical CHP | | | | [H2SO4], ppm | CHP conversion in reactors, % | | | Temperature in reactors, °C. | | | Mole Ratio: phenol:acetone: cumene | Amount of added acetone, % |
|---|---|---|---|---|---|---|---|---|---|---|---|---|---|---|
| | | CHP | DMBA | Aceto- phenone | Cumene | | A | B | C | A | B | C | | |
| 1 | 72 | 82.9 | 4.2 | 0.6 | 12 | 250 | 65 | 89.6 | 94.5 | 75.8 | 72.4 | 63.1 | 1:1.42:0.22 | 12.16 |
| 2 | 72 | 82.9 | 4.2 | 0.6 | 12 | 200 | 50 | 69 | 81.2 | 48.2 | 48.3 | 49.1 | 1:1.28:0.22 | 8 |
| 3 | 72 | 90.3 | 6.2 | 1 | 2 | 200 | 49.6 | 67 | 78.9 | 48.5 | 49.5 | 50 | 1:1.28:0.22 | 8 |
| 4 | 72 | 82.9 | 4.2 | 0.6 | 12 | 180 | 48.8 | 67 | 79.6 | 48.4 | 49.1 | 49.9 | 1:1.28:0.22 | 8 |
| 5 | 72 | 82.9 | 4.2 | 0.6 | 12 | 180 | 50 | 68.8 | 81.7 | 47 | 48.3 | 48.9 | 1:1.19:0.22 | 5 |
| 6 | 90 | 82.9 | 4.2 | 0.6 | 12 | 180 | 44 | 67 | 77.1 | 50 | 50 | 48.6 | 1:1.19:0.22 | 5 |
| 7 | 54 | 82.9 | 4.2 | 0.6 | 12 | 180 | 50 | 72.9 | 81.9 | 50 | 49.2 | 49 | 1:1.19:0.22 | 5 |
| 8 | 72 | 82.9 | 4.2 | 0.6 | 12 | 180 | 50 | 69 | 81.2 | 48.2 | 48.3 | 49.1 | 1:1.19:0.22 | 5 |
| 9 | 72 | 82.9 | 4.2 | 0.6 | 12 | 180 | 50 | 69 | 81.2 | 48.2 | 48.3 | 49.1 | 1:1.19:0.22 | 5 |
| 10 | 72 | 82.9 | 4.2 | 0.6 | 12 | 200 | 50 | 69 | 81.2 | 48.2 | 48.3 | 49.1 | 1:1.19:0.22 | 8 |
| 11 | 72 | 82.9 | 4.2 | 0.6 | 12 | 200 | 50 | 69 | 81.2 | 48.2 | 48.3 | 49.1 | 1:1.19:0.22 | 8 |

EXAMPLE SUMMARY TABLE 2
2nd Stage -- DCP Cleavage

| Exp. No. | [H2SO4], ppm | [H2O] wt. % | [DCP] outlet wt, % | Temp., °C. | AMS Yield, % |
|---|---|---|---|---|---|
| 1 | 250 | 1.91 | 0.08 | 99 | 78.6 |
| 2 | 100 | 1.4 | 0.05 | 120–137 | 85.6 |
| 3 | 100 | 1.4 | 0.05 | 120–143 | 85.1 |
| 4 | 90 | 1.4 | 0.05 | 120–137 | 85.8 |
| 5 | 90 | 1.4 | 0.05 | 120–137 | 85.7 |
| 6 | 90 | 1.4 | 0.05 | 120–137 | 85.6 |
| 7 | 90 | 1.4 | 0.05 | 120–137 | 85.5 |
| 8 | 90 | 2 | 0.05 | 127–146 | 87 |
| 9 | 90 | 1.7 | 0.05 | 123–140 | 86.4 |
| 10 | 100 | 2 | 0.05 | 127–146 | 86.8 |
| 11 | 100 | 1.7 | 0.05 | 123–140 | 89.7 |

The terms and expressions which have been employed are used as terms of description and not of limitation, and there is no intention in the use of such terms and expressions of excluding any equivalent of the features shown and described or portions thereof, it being recognized that various modifications are possible within the scope of the invention.

We claim:

1. A process for cleaving technical CHP containing DMBA to phenol, acetone and α-methylstyrene comprising:
   introducing technical grade CHP into at least the first of a series of at least three sequential reactors;
   cleaving CHP in said least three sequential reactors under substantially isothermal conditions in a temperature range of about 47–50° C. to produce a first product stream at a first temperature, said product stream containing DCP;
   heating the first product stream to a second temperature of about 50–55° C. higher than said first temperature, thus producing a heated first product stream;
   introducing the heated first product stream into a plug-flow reactor wherein DCP is decomposed to a mixture containing phenol, acetone and α-methylstyrene; and
   introducing a first acetone stream of into said least the first of a series of at least three sequential reactors and introducing a second acetone stream into said plug-flow reactor, wherein said first and second acetone streams differ in quantity of delivered acetone.

2. The process of claim 1 wherein each of the at least three reactors is operated at a pressure of from 1 to 10 atmospheres.

3. The process of claim 1 wherein the temperature in the first reactor is in the range of 47–50° C., the temperature in the second reactor is 48–50° C. and the temperature in the third reactor is 48–50° C.

4. The process of claim 1 wherein the CHP conversion in the first reactor is 43–50%, in the second reactor is 67–73% and in the third reactor is 78–82%.

5. The process of claim 1 wherein DCP is decomposed in a multi-section plug flow reactor.

6. The process of claim 1 wherein the cleaving of the CHP is done under the influence of a acidic catalyst, preferably sulfuric acid, present in an amount from about 0.018 to about 0.020 wt.-%.

7. The process of claim 1 wherein the DCP cleavage is conducted under non-isothermal conditions.

8. The process of claim 7 wherein the DCP cleavage is conducted at a temperature of from about 120 to about 146° C.

9. The process of claim 5 wherein the temperature is controlled in each section of the multi-section plug-flow reactor.

10. The process of claim 9 wherein the temperature is controlled by obtaining a temperature profile over each section of the plug-flow reactor and comparing the obtained profile with a pre-established temperature profile for the respective section of the reactor.

11. The process of claim 10 wherein in response to detected deviations, at least one of an amount of water fed to the plug-flow reactor, the temperature, or the degree of conversion of sulfuric acid into $NH_4SO_4$ is adjusted.

12. The process of claim 1 wherein said first acetone stream is in an amount of 5 to 8 wt.-% relative to the CHP flow rate.

13. The process of claim 1 wherein said second acetone stream is in an amount of 8 to 16 wt.-%, relative to the flow rate of CHP.

14. A system for cleaving technical CHP to form phenol, acetone and α-methylstyrene comprising:
   a supply line for supplying a feed stream containing CHP;
   a first stage into which said feed stream is introduced, said first stage comprising a series of mixing reactors wherein the CHP is cleaved to produce a product stream;
   a second supply line for supplying a first additional acetone stream to said first stage;

a recycle system whereby at least a portion of the product stream is split off from the remainder of said product stream;

a mixing tank for receiving the remainder of said product stream with means for optionally introducing other materials into said tank;

at least one heat exchanger for increasing the temperature of the remaining product stream by about 50–55° C.;

a multi-stage plug flow reactor into which the heated product stream is introduced and wherein DCP is cleaved;

a third supply line for supplying a second additional acetone stream to said second stage, wherein said first and second additional acetone streams differ in quantity of delivered acetone; and a temperature measuring and control system adapted to control the temperature increase in each stage of said multi-step reactor.

15. A two stage process for cleaving technical CHP containing DMBA to phenol, acetone and α-methylstyrene comprising:

introducing technical grade CHP into a first stage, said first stage comprising at least a first, second and third reactor, said least first, second and third reactor being in series;

introducing a first acetone stream into said first stage;

cleaving CHP in said reactors tinder substantially isothermal conditions wherein the first reactor operates at a temperature of 47–50° C. and provides a CHP conversion of 43–50%, the second reactor operates at a temperature of 48–50° C. and provides a CHP conversion of 67–73%, and the third reactor operates at a temperature of 48–50° C. and provides a CHP conversion of 78–82% and producing a first product stream at a first temperature, said product stream containing DCP;

introducing the first product stream into a second stage, said second stage comprising a reactor wherein DCP is decomposed to a mixture containing phenol, acetone and α-methylstyrene under non-isothermal conditions; and introducing a second acetone stream into said second stage.

16. The process of claim 15 wherein the first product stream is heated to a second temperature of about 50–55° C. higher than said first temperature prior to it being introduced into said second stage.

17. The process of claim 15 wherein said first acetone stream is in an amount of 5–8 relative % on the basis of 1 ton technical CHP.

18. The process of claim 17 wherein the cleavage of DCP is conducted in the second stage in the plug-flow reactor and wherein said second acetone stream is in an amount of 8–16 relative % of acetone on the basis of 1 ton technical CHP.

19. The process of claim 18 wherein the weight ratio of said first acetone stream and said second acetone stream is 1:1 to 1:3.

20. The process of claim 19 wherein acetone added to the reactors of the first and second stages via said first and second acetone streams is removed in an evaporator under a vacuum of 200–600 mm Hg and, is condensed in a cooler, and is recycled to the reactors of the first and second stages.

21. The process of claim 18 where crude acetone from distillation of acetone columns is used as said first and second acetone streams fed to the first and second stages.

22. The process of claim 15 wherein the cleavage of DCP is conducted non-isothermally under a controlled temperature rise of from about 120° C. to 146° C.

23. The process of claim 15 wherein the concentration of $H_2SO_4$ as a catalyst is 0.018–0.020% of mass at the first stage and 0.005 to 0.008% of mass maintained at the second stage.

24. The process of claim 15 wherein the DCP conversion at the second stage is controlled by a change, optionally simultaneously, of water concentration in the reaction medium, degree of sulfuric acid transfer to $NH_4HSO_4$ and temperature due to the installation of a thermocouple in each section of the reactor and by comparison of the obtained temperature profile with that required by a kinetic model.

25. The process of claim 24 wherein the temperature profile is controlled in each section of the DCP reactor based on temperature measurement.

26. The process of claim 25 wherein the concentration of unreacted DCP after the reactor of the second stage is from 0.05 wt % to 0.10 wt %.

27. The process of claim 20 wherein an aqueous ammonia solution is added to the evaporator to convert $H_2SO_4$ to a neutral salt $(NH_4)_2SO_4$ in order to lower the unselective losses of desired products while evaporating acetone.

28. The process of claim 1, wherein CHP cleavage regime is conducted in accordance with a plug-flow reactor regime.

29. The process of claim 28, wherein to facilitate the plug-flow regime for CHP cleavage, each of the three sequential reactors comprises a plurality of baffles.

30. The process of claim 29, wherein the plurality of baffles comprises 6–16 baffles.

31. The process of claim 29, wherein a magnitude of a circulation ratio of cleavage products with respect to technical CHP is maintained at approximately 8–40:1.

* * * * *